(12) United States Patent
Namose et al.

(10) Patent No.: US 6,642,521 B2
(45) Date of Patent: Nov. 4, 2003

(54) METHOD FOR MEASURING GREENHOUSE GASES USING INFRARED ABSORPTION SPECTROMETER

(75) Inventors: Isamu Namose, Suwa (JP); Toshikazu Sugiura, Suwa (JP)

(73) Assignee: Seiko Epson Corporation, Tokyo (JP)

( * ) Notice: Subject to any disclaimer, the term of this patent is extended or adjusted under 35 U.S.C. 154(b) by 142 days.

(21) Appl. No.: 09/944,191

(22) Filed: Sep. 4, 2001

(65) Prior Publication Data

US 2002/0060292 A1 May 23, 2002

(30) Foreign Application Priority Data

Sep. 6, 2000 (JP) ........................................ 2000-270684

(51) Int. Cl.[7] .............................................. G01N 33/18
(52) U.S. Cl. ................. 250/339.09; 250/338.1
(58) Field of Search .................. 250/339.09, 338.1; 436/133, 150; 422/84

(56) References Cited

U.S. PATENT DOCUMENTS

| | | | | |
|---|---|---|---|---|
| 5,910,448 A | * | 6/1999 | Atwater et al. | 436/133 |
| 6,452,179 B1 | * | 9/2002 | Coates et al. | 250/339.09 |
| 6,455,850 B1 | * | 9/2002 | Coates et al. | 250/338.1 |
| 2001/0031224 A1 | * | 10/2001 | Labuda et al. | 422/84 |
| 2003/0015019 A1 | * | 1/2003 | O'Brien | 73/23.2 |

OTHER PUBLICATIONS

J. Mayers et al. "Emissions Characterization Package", (Formerly Process Tool Effluent Characterization) I300I Expectations, Rev. 2.4–b (generally referred to as "Intel Protocol") Intel Corportion, which was distributed at Global Semiconductor Industry Conference on Perfluorocompound Emissions Control that was held in Monterey, California, U.S. in Apr. 1998.

J. Mayers et al. "Equipment Environmental Characterization Guidelines", Rev. 3.0, pp. 4–39, Intel Corportion, which was distributed at Global Semiconductor Industry Conference on Perfluorocompound Emissions Control that was held in Monterey, California, U.S. in Apr. 1998.

* cited by examiner

*Primary Examiner*—Constantine Hannaher
*Assistant Examiner*—Otilia Gabor
(74) *Attorney, Agent, or Firm*—Oliff & Berridge PLC

(57) ABSTRACT

The invention provides a method for measuring PFC components in a discharged gas with ease and good reproducibility, using an FT-IR. The method for measuring greenhouse gases using an infrared absorption spectrometer in accordance with the present invention includes the steps of selecting a process chemical material, selecting a measurement target chemical material corresponding to the process chemical material, designating expected concentration ranges for the process chemical material and the measurement target chemical material, selecting libraries for the respective expected concentration ranges for the process chemical material and the measurement target chemical material, and analyzing data obtained by a gas infrared absorption spectrometry based on the libraries.

16 Claims, 14 Drawing Sheets

Atmosphere
16: Harmful sabstance removal apparatus
22: Pressure sensor
23: Temperature sensor Atmosphere 16: Harmful sabstance removal apparatus
22: Pressure sensor
23: Temperature sensor

| Molecular Formula | Process chemical material? | Expected concentration range | | Selected library | Selected peak region (cm-1) |
|---|---|---|---|---|---|
| CF4 | ☐ | ~10ppm-m | ▶ | CF4_10A | 1230-1305 |
| CHF3 | ☐ | ~10ppm-m | ▶ | TFM_10A | 1090-1247 |
| C2F4 | ☐ | 0~ ppm-m | ▶ | C2F4_4A | 1161-1212 |
| C2F6 | ☐ | 30~100ppm-m | ▶ | C2F6_31A | 1082-1136 |
| C3F8 | ☐ | 0~ ppm-m | ▶ | C3F8_3A | 956-1061 |
| C4F8 | ☐ | 0~ ppm-m | ▶ | C4F8_1A | 920-1020 |
| SF6 | ☐ | 0~ ppm-m | ▶ | SF6Z_19A | 910-1009 |
| NF3 | ☐ | 0~ ppm-m | ▶ | NF3_31A | 832-960 |
| CO | | 0~ ppm-m | ▶ | CO_31A | 2143-2246 |
| CO2 | | 0~ ppm-m | ▶ | CO2_51A | 2280-2390 |
| COF2 | | 0~ ppm-m | ▶ | COF2_55A | 1790-2015 |
| HF | | 0~ ppm-m | ▶ | HF_30A | 4032-4080 |
| SiF4 | | 0~ ppm-m | ▶ | SIF4_38A | 1000-1058 |
| SOF2 | | 0~ ppm-m | ▶ | SOF2_17A | 712-860 |
| SO2F2 | | 0~ ppm-m | ▶ | SO2F2_1A | 1445-1545 |
| SO2 | | 0~ ppm-m | ▶ | SO2_3A | 1290-1415 |
| NO | | ~500ppm-m | ▶ | NO_27A | 1757-1990 |
| NO2 | | 0~ ppm-m | ▶ | NO2_19A | 1525-1791 |
| N2O | | 0~ ppm-m | ▶ | N2O_10A | 1216-1338 |

Fig. 2

| Molecular Formula | | Process chemical material? | Expected concentration range | | Selected library | Selected peak region (cm-1) |
|---|---|---|---|---|---|---|
| CF4 | ☐ | Measurement target chemical material | ~10ppm-m | ▶ | CF4_10A | 1230-1305 |
| CHF3 | ☐ | Measurement target chemical material | ~10ppm-m | ▶ | TFM_10A | 1090-1247 |
| C2F4 | ☐ | Measurement target chemical material | 0~ ppm-m | ▶ | C2F4_4A | 1181-1212 |
| C2F6 | ☐ | Measurement target chemical material | 30~100ppm-m | ▶ | C2F6_31A | 1082-1136 |
| C3F8 | ☐ | Measurement target chemical material | 0~ ppm-m | ▶ | C3F8_3A | 956-1061 |
| C4F8 | ☑ | Process chemical material | 0~ ppm-m | ▶ | C4F8_1A | 920-1020 |
| SF6 | ☐ | | 0~ ppm-m | ▶ | SF6Z_19A | 910-1009 |
| NF3 | | | 0~ ppm-m | ▶ | NF3_31A | 832-960 |
| CO | | Measurement target chemical material | 0~ ppm-m | ▶ | CO_31A | 2143-2246 |
| CO2 | | Measurement target chemical material | 0~ ppm-m | ▶ | CO2_51A | 2280-2390 |
| COF2 | | Measurement target chemical material | 0~ ppm-m | ▶ | COF2_55A | 1790-2015 |
| HF | | Measurement target chemical material | 0~ ppm-m | ▶ | HF_30A | 4032-4080 |
| SiF4 | | Measurement target chemical material | 0~ ppm-m | ▶ | SIF4_38A | 1000-1058 |
| SOF2 | | | 0~ ppm-m | ▶ | SOF2_17A | 712-860 |
| SO2F2 | | | 0~ ppm-m | ▶ | SO2F2_1A | 1445-1545 |
| SO2 | | | 0~ ppm-m | ▶ | SO2_3A | 1290-1415 |
| NO | | | ~500ppm-m | ▶ | NO_27A | 1757-1990 |
| NO2 | | | 0~ ppm-m | ▶ | NO2_19A | 1525-1791 |
| N2O | | | 0~ ppm-m | ▶ | N2O_10A | 1216-1338 |

Fig. 3

| Molecular Formula | Process chemical material? | | Expected concentration range | | Selected library | Selected peak region (cm-1) |
|---|---|---|---|---|---|---|
| CF4 | ☐ | Measurement target chemical material | ~10ppm-m | ▶ | CF4_10A | 1230-1305 |
| CHF3 | ☐ | Measurement target chemical material | 60~ ppm-m | ▶ | TFM_60A | 2980 - 3080 |
| C2F4 | ☐ | Measurement target chemical material | 0~ ppm-m | ▶ | C2F4_4A | 1161-1212 |
| C2F6 | ☐ | Measurement target chemical material | 30~100ppm-m | ▶ | C2F6_31A | 1082-1136 |
| C3F8 | ☐ | Measurement target chemical material | 0~ ppm-m | ▶ | C3F8_3A | 956-1061 |
| C4F8 | ☑ | Process chemical material | 0~ ppm-m | ▶ | C4F8_1A | 920-1020 |
| SF6 | ☐ | | 0~ ppm-m | ▶ | SF6Z_19A | 910-1009 |
| NF3 | ☐ | | 0~ ppm-m | ▶ | NF3_31A | 832-960 |
| CO | | Measurement target chemical material | 0~ ppm-m | ▶ | CO_31A | 2143-2246 |
| CO2 | | Measurement target chemical material | 0~ ppm-m | ▶ | CO2_51A | 2280-2390 |
| COF2 | | Measurement target chemical material | 0~ ppm-m | ▶ | COF2_55A | 1790-2015 |
| HF | | Measurement target chemical material | 0~ ppm-m | ▶ | HF_30A | 4032-4080 |
| SiF4 | | Measurement target chemical material | 0~ ppm-m | ▶ | SIF4_38A | 1000-1058 |
| SOF2 | | | 0~ ppm-m | ▶ | SOF2_17A | 712-860 |
| SO2F2 | | | 0~ ppm-m | ▶ | SO2F2_1A | 1445-1545 |
| SO2 | | | 0~ ppm-m | ▶ | SO2_3A | 1290-1415 |
| NO | | | ~500ppm-m | ▶ | NO_27A | 1757-1990 |
| NO2 | | | 0~ ppm-m | ▶ | NO2_19A | 1525-1791 |
| N2O | | | 0~ ppm-m | ▶ | N2O_10A | 1216-1338 |

Fig. 4

| Molecular Formula | Process chemical material? | | Expected concentration range | | Selected library | Selected peak region (cm-1) |
|---|---|---|---|---|---|---|
| CF4 | ☐ | Measurement target chemical material | ~10ppm-m | ▶ | CF4_10A | 1230-1305 |
| CHF3 | ☑ | Measurement target chemical material | 10-60ppm-m | ▶ | TFM_10A,60A,16A | 1090-1247, 1316-1437, 2980-3080 |
| C2F4 | ☐ | Measurement target chemical material | 0~ ppm-m | ▶ | C2F4_4A | 1161-1212 |
| C2F6 | ☐ | Measurement target chemical material | 30~100ppm-m | ▶ | C2F6_31A | 1082-1136 |
| C3F8 | ☐ | Measurement target chemical material | 0~ ppm-m | ▶ | C3F8_3A | 956-1061 |
| C4F8 | ☑ | Process chemical material | 0~ ppm-m | ▶ | C4F8_1A | 920-1020 |
| SF6 | ☐ | | 0~ ppm-m | ▶ | SF6Z_19A | 910-1009 |
| NF3 | ☐ | | 0~ ppm-m | ▶ | NF3_31A | 832-960 |
| CO | | Measurement target chemical material | 0~ ppm-m | ▶ | CO_31A | 2143-2246 |
| CO2 | | Measurement target chemical material | 0~ ppm-m | ▶ | CO2_51A | 2280-2390 |
| COF2 | | Measurement target chemical material | 0~ ppm-m | ▶ | COF2_55A | 1790-2015 |
| HF | | Measurement target chemical material | 0~ ppm-m | ▶ | HF_30A | 4032-4080 |
| SiF4 | | Measurement target chemical material | 0~ ppm-m | ▶ | SIF4_38A | 1000-1058 |
| SOF2 | | | 0~ ppm-m | ▶ | SOF2_17A | 712-860 |
| SO2F2 | | | 0~ ppm-m | ▶ | SO2F2_1A | 1445-1545 |
| SO2 | | | 0~ ppm-m | ▶ | SO2_3A | 1290-1415 |
| NO | | | ~500ppm-m | ▶ | NO_27A | 1757-1990 |
| NO2 | | | 0~ ppm-m | ▶ | NO2_19A | 1525-1791 |
| N2O | | | 0~ ppm-m | ▶ | N2O_10A | 1216-1338 |

Fig. 5

METHOD FOR MEASURING GREENHOUSE GASES USING INFRARED ABSORPTION SPECTROMETER

BACKGROUND OF THE INVENTION

1. Field of Invention

The present invention relates to a method for measuring greenhouse gases using an infrared absorption spectrometer. More particularly, the present invention relates to a method for measuring greenhouse gases using a Fourier-transform infrared spectroscope (FT-IR).

2. Description of Related Art

In recent years, problems relating to global warming are attracting more attention while greater concerns in environmental problems being raised. Global warming progresses in association with increases in the concentration of greenhouse effect gases (or greenhouse gases) in the atmosphere, such as $CO_2$, NOx, methane, PFC (perfluorocarbon) and the like. These greenhouse gases have strong absorbance in an infrared region. When discharged into the atmosphere, they absorb energy irradiated from the earth's surface. The absorbed energy is radiated upward toward outer space and downward toward the earth's surface. In this instance, a part of the energy radiated from the earth's surface is returned again to the earth's surface by the greenhouse gases, such that the temperature on the earth's surface increases. By this system, the greenhouse gases are thought to bring about a global warming effect.

Global warming potential (GWP) is known as an indicator to compare degrees of the global warming effect caused by the greenhouse gases. The GWP represents how much warming effect one unit weight of a gas has compared to one unit of $CO_2$. PFCs are counted as gases having a high global warming effect among the greenhouse gases. PFCs have an extremely high GWP value. For example, the GWP value of $CF_4$ is about 6,500 times higher than that of $CO_2$. Also, PFC is stable compared to other gases, and have a very long life in the atmosphere. For example, the life of $CF_4$ in the atmosphere is about 50,000 years. Therefore, once discharged into the atmosphere, PFC would warm the earth for many years.

The PFCs are ordinarily used in a process of manufacturing semiconductor devices, and more particularly, they are frequently used in an apparatus using low-pressure plasma. For example, in a dry etching apparatus, PFCs, such as $CF_4$, $C_4F_8$ and the like, are used to etch $SiO_2$ and $Si_3N_4$. Also, in a CVD apparatus, gas plasma of $C_2F_6$ or the like is often used to clean films of silicon compound or the like adhered to the apparatus. Furthermore, a liquid PFC is used as a medium to cool wafers. However, as described above, since the PFC has a high global warming effect, the reduction in the discharged amount of PFCs is purposefully being pursued. At the COP3 Kyoto Conference that was held in December 1997, an agreement was reached to reduce the discharged amount of PFCs and the like in Japan by 6% by the year 2010 compared to the level in the year 1995. Thereafter, at the ESH (environment·safety·health) task force in the WSC (World Semiconductor Conference) held in 1999, an agreement was reached to reduce the total discharged amount by 10% by the year 2010 compared to the level in the year 1995.

In order to verify the reduction of the discharged amount of PFCs, PFC gases that are emitted from factories need to be measured. At present, since it is difficult to measure PFC gases emitted from a factory, PFC gases discharged from a semiconductor manufacturing apparatus that uses PFCs are measured, and the discharged amount of PFCs is determined using an amount ratio (emission factor) of discharged gases to fed gases, and the amount of gases that are consumed in the factory. PFC gases that are actually discharged from a semiconductor manufacturing apparatus are measured to calculate the emission factor. Measurements of PFC gases that are actually discharged from semiconductor manufacturing apparatuses are conducted according to guidelines referred to as "Emissions Characterization Package Rev. 2.4 (generally referred to as "Intel Protocol") (currently, "Equipment Environmental Characterization Guidelines Rev. 3.0") by J. Mayers et al. of Intel Corporation, which was distributed at Global Semiconductor Industry Conference on Perfluorocompound Emissions Control that was held in Monterey, Calif., U.S. in April 1998. The Intel Protocol describes a method for measuring emitted PFC gases, using a quadrupole mass analyzing spectrometer (QMAS) and a Fourier-transform infrared spectroscope (FT-IR). However, since no detailed description is provided for the measurements using the FT-IR, measurement results may have great variations depending on measurement methods. Accordingly, to compensate for the Intel Protocol, methods of measuring PFCs in emitted gasses with simpler processes and good reproducibility have been sought.

SUMMARY OF THE INVENTION

It is an object of the present invention to provide a method for measuring components in emitted gases with ease and good reproducibility, using an infrared absorption spectrometer.

(A) A method for measuring greenhouse gases using an infrared absorption spectrometer in accordance with the present invention includes the steps of:

selecting a process chemical material;

selecting a measurement target chemical material corresponding to the process chemical material:

designating expected concentration ranges for the process chemical material and the measurement target chemical material;

selecting libraries for the respective expected concentration ranges for the process chemical material and the measurement target chemical material; and analyzing data obtained by a gas infrared absorption spectrometry based on the libraries.

The process chemical material is a chemical material that is used in a process. Also, the measurement target chemical material is a chemical material that may possibly be included in the gas because the process chemical material is included in the gas.

Also, the library is absorbance data that is measured in advance for known concentration of the chemical material, which is used to perform an accurate concentration measurement, when data obtained by an infrared absorption spectrometry of the chemical material is analyzed.

By the method for measuring greenhouse gases in accordance with the present invention, concentrations of respective components in a mixed gas can be measured with a simplified method and with good accuracy.

For the method for measuring greenhouse gases in accordance with the present invention, the following description is provided of exemplary embodiments (1)~(3).

(1) A library formed of absorbance data for a plurality of known concentrations is made for each chemical material in the gas;

calibration curve data with respect to concentration-absorption area for a main peak region and an auxiliary peak region is made for the each chemical material in the gas based on the library; and data obtained by the gas infrared absorption spectrometry is analyzed based on the calibration curve data.

When the expected concentration range of each composition among the gas is included in a region where a linearity of the calibration curve data for the main peak region is small, the concentration is determined using the calibration curve data for the auxiliary peak region.

Here, the "main peak region" is a region that includes the highest peak in the infrared absorption waveform of the gas. Also, the "auxiliary peak region" is a region that includes a peak located in a region that is different from the main peak region. Depending on compositions, two or more auxiliary peak regions may exist.

Also, the "calibration curve data" is data representing the relation between concentrations and absorption areas for each component in the gas. When an infrared absorption measurement is conducted, libraries are selected in accordance with the expected concentration ranges, and data analysis is conducted based on calibration curve data for the selected libraries.

Also, the "region where a linearity of the calibration curve data for the main peak region is small" is an area in the calibration curve data for the main peak region that has a smaller linearity in the relation between concentrations and absorption areas, compared to the calibration curve data for the auxiliary peak region. By the method described above, the calibration curve data for the auxiliary peak region is used to determine the concentration described above, with the result that concentration of each of the components in the gas can be measured with high accuracy.

Alternatively, when the expected concentration range of each composition among the gas is included in a region where a linearity of the calibration curve data for the auxiliary peak region is small, the concentration is determined using the calibration curve data for the main peak region. Here, the "region where a linearity of the calibration curve data for the auxiliary peak region is small" is an area in the calibration curve data for the auxiliary peak region that has a small linearity in the relation between concentrations and absorption areas, compared to the calibration curve data for the main peak region.

By the method described above, the calibration curve data for the main peak region is used to determine the concentration described above, with the result that concentration of each of the components in the gas can be measured with high accuracy Also, in this case, the concentration may be determined using both of the calibration curve data for the main peak region and the calibration curve data for the auxiliary peak region.

(2) The process chemical material may include at least one of $CF_4$, $CHF_3$, $C_2F_4$, $C_2F_6$, $C_3F_8$, $C_4F_8$, $C_5F_8$, HF, $SiF_4$, $NF_3$, $SF_6$ and $N_2O$.

(3) The measurement target chemical material may include at least one of $CF_4$, $CHF_3$, $C_2F_4$, $C_2F_6$, $C_3F_8$, $C_4F_8$, $C_5F_8$, $COF_2$, HF, $SiF_4$, $OF_2$, $NF_3$, $SO_2$, $SF_6$, $SO_2F_2$, $SOF_2$, NO, $N_2O$, $NO_2$, CO and $CO_2$.

(B) A method for measuring greenhouse gases using an infrared absorption spectrometer in accordance with another aspect of the present invention is a method in which, when data for gas obtained by an infrared absorption spectrometry is analyzed, a calibration curve representing absorption areas with respect to concentrations is made for each of a main peak region and an auxiliary peak region for each component in the gas. When a concentration of each composition among the gas is expected to be included in a region where a linearity of the calibration curve for the main peak region is small, the concentration is determined using the calibration curve data for the auxiliary peak region. By the method, the effects described above can be obtained.

(C) A method for measuring greenhouse gases using an infrared absorption spectrometer in accordance with yet another aspect of the present invention is a method in which, when data for gas obtained by an infrared absorption spectrometry is analyzed, a calibration curve representing absorption areas with respect to concentrations is made for each of a main peak region and an auxiliary peak region for each component in the gas. When a concentration of each composition among the gas is expected to be included in a region where a linearity of the calibration curve for the auxiliary peak region is small, the concentration is determined using the calibration curve for the main peak region. By the method, the effects described above can be obtained.

In either of methods (B) and (C) described above, the concentration may be determined using both of the calibration curve for the main peak region and the calibration curve for the auxiliary peak region.

Also, for a portion of the calibration curve having a low linearity, a correction to increase measurement points adjacent the portion may be performed with respect to the calibration curve.

Here, the "measurement point" is data representing a value of an absorption area with respect to a specified concentration for each composition in the gas. The "portion of the calibration curve having a low linearity" is a portion that is deviated from an equation that represents a specified relation to be established between concentrations and absorption areas for each of the components in the gas. By performing the correction, the linearity of the calibration curve can be increased. As a result, by analyzing data based on the data with respect to the corrected calibration curve (calibration curve data), the concentration of components included in the gas can be accurately calculated.

Also, for a portion of the calibration curve having a high linearity, the calibration curve may be made using one measurement point or two measurement points in the portion having a high linearity. By the method, a highly accurate calibration curve can be made even with fewer measurement points.

(D) A method for measuring greenhouse gases using an infrared absorption spectrometer in accordance with yet another aspect of the present invention includes the steps of:

analyzing data based on an absorption waveform for a gas obtained by an infrared absorption spectrometry;

measuring components on priority basis, among components in the gas, having peaks that do not overlap peaks of the other components; and successively subtracting the peaks of the components from the absorption waveform.

By the method, even when peaks concur with one another or overlap one another for each of the components, the concentration of each of the components can be accurately measured.

In this case, the following steps (a)–(j) can be performed in the method:

(a) subtracting peaks of NO and $SO_2F_2$ from the absorption waveform of the gas to measure NO and $SO_2F_2$;

(b) subtracting a peak of $COF_2$ from the absorption waveform obtained in the step (a) to measure $COF_2$;

(c) subtracting a peak of $SOF_2$ from the absorption waveform obtained in the step (b) to measure $SOF_2$;

(d) subtracting a peak of $OF_2$ from the absorption waveform obtained in the step (c) to measure $OF_2$;

(e) subtracting peaks of $SF_6$, $NF_3$ and $C_4F_8$ from the absorption waveform obtained in the step (d) to measure $SF_6$, $NF_3$ and $C_4F_8$, respectively;

(f) subtracting peaks of $C_3F_8$ and $SiF_4$ from the absorption waveform obtained in the step (e) to measure $C_3F_8$ and $SiF_4$, respectively;

(g) subtracting peaks of $N_2O$, $C_2F_6$ and $C_2F_4$ from the absorption waveform obtained in the step (f) to measure $N_2O$, $C_2F_6$ and $C_2F_4$, respectively;

(h) subtracting peaks of $CF_4$, $SO_2$ and $CO$ from the absorption waveform of the gas obtained in the step (g) to measure $CF_4$, $SO_2$ and $CO$, respectively;

(i) measuring $CHF_3$ from the absorption waveform obtained in the steps (a)~(h); and (j) subtracting peaks of HF, $CO_2$ and $NO_2$ from any one of the absorption waveform of the gas and the absorption waveforms of the gas obtained in the steps (a)~(i).

Furthermore, in this case, in addition to the above steps (a)~(j), one or two or more of the following steps (1)~(8) may be performed.

(1) HF, $CO_2$ and $NO_2$ are measured by any one of the steps (a)~(i) instead of the step (j), or by the step that is different from the steps (a)~(i) but is conducted before the step (j).

(2) $SF_6$ is measured by any one of the steps (f)~(j) instead of the step (e), or by the step that is different from the steps (f)~(j) but is conducted after the step (e).

(3) $CF_4$ is measured by the step (i) or the step (j) instead of the step (h), or by the step that is different from the step (i) or the step (j) but is conducted after the step (h).

(4) $SiF_4$ is measured by any one of the steps (g)~(j) instead of the step (f), or by the step that is different from the steps (g)~(j) but is conducted after the step (f).

(5) CO is measured by the step (i) or the step (j) instead of the step (h), or by the step that is different from the step (i) or the step (j) but is conducted after the step (h).

(6) $C_2F_6$ is measured by any one of the steps (h)~(j) instead of the step (g), or by the step that is different from the steps (h)~(j) but is conducted after the step (g).

(7) $C_2F_4$ is measured by any one of the steps (h)~(j) instead of the step (g), or by the step that is different from the steps (h)~(j) but is conducted after the step (g).

(8) $C_4F_8$ is measured by the step (f) instead of the step (e), or by the step that is different from the step (f) but is conducted after the step (d) but before the step (g).

(E) In a method for measuring greenhouse gases using an infrared absorption spectrometer in accordance with yet another aspect of the present invention, when an infrared absorption spectrometry is conducted for a gas, one or more of components in the gas may be used as correction gases.

In the method described above, a plurality of values for concentrations of the correction gases to be used for correction may be set at equal intervals as viewed in logarithmic values of the concentrations. By the method, since the measurement points can be disposed at equal intervals on logarithmic scale, a highly accurate calibration curve can be made with fewer measurement points.

Also, when $CF_4$ or $SF_6$ is selected as the correction gas, a calibration curve representing absorption areas for concentrations with respect to a main peak region regarding the correction gas can be made, and a correction can be made at a portion having excellent linearity in the calibration curve with respect to the main peak region. By the method, a highly accurate correction can be conducted.

In accordance with the present invention, the gas that is subject to a measurement using an infrared absorption spectrometer may include at least one of $CF_4$, $CHF_3$, $C_2F_4$, $C_2F_6$, $C_3F_8$, $C_4F_8$, $C_5F_8$, $COF_2$, HF, $SiF_4$, $OF_2$, $NF_3$, $SO_2$, $SF_6$, $SO_2F_2$, $SOF_2$, NO, $N_2O$, $NO_2$, CO and $CO_2$.

BRIEF DESCRIPTION OF THE DRAWINGS

FIG. 2 schematically shows a calculation sheet that is used to select measurement target chemical materials by a process using a computer based on a selected process chemical material in the discharged gas.

FIG. 3 schematically shows contents of the process on the calculation sheet displayed on a display.

FIG. 4 schematically shows contents of the process on the calculation sheet displayed on a display.

FIG. 5 schematically shows contents of the process on the calculation sheet displayed on a display.

DETAILED DESCRIPTION OF PREFERRED EMBODIMENTS

Preferred embodiments of the present invention will be described below with reference to the accompanying drawings.

(Outline of Measurement System)

Figure 1:
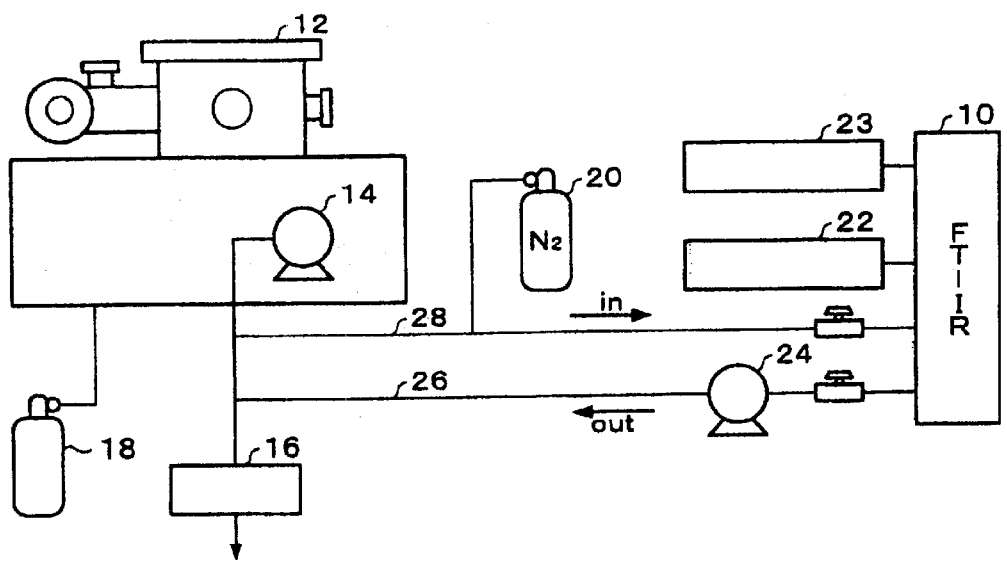
FIG. 1 schematically shows a gas measurement system in accordance with one embodiment of the present invention.

One embodiment of the present invention is described with reference to an example of a method in which an FT-IR is used to measure components of gas that is discharged from a dry etching apparatus that uses $C_4F_8$. FIG. 1 schematically shows a gas measurement system in accordance with the embodiment.

When PFC gas is used, it is possible that the discharged gas may contain $CF_4$, $CHF_3$, $C_2F_4$, $C_2F_6$, $C_3F_8$, $C_4F_8$, $C_5F_8$, $COF_2$, HF, $SiF_4$, $OF_2$, $NF_3$, $SO_2$, $SF_6$, $SO_2F_2$, $SOF_2$, NO, $N_2O$, $NO_2$, CO and $CO_2$.

For example, when gas plasma of $C_4F_8$ is generated in a chamber 12 of the dry etching apparatus, the chamber 12 of the dry etching apparatus is brought substantially to a vacuum state using a pump, and then a specified amount of $C_4F_8$ is introduced and a high voltage is applied. As a result, gas plasma of $C_4F_8$ is generated. The gas plasma is used for a CVD. In this case, a certain portion of the $C_4F_8$ used for the CVD is dissolved into $CF_4$ and the like, but the remaining portion is discharged as $C_4F_8$ from the chamber 12. The discharged gas is pumped in by a pump 14, the discharged gas is diluted with $N_2$ gas that is supplied from an $N_2$ source 20, and then introduced in an FT-IR 10, wherein infrared absorption of each of the components in the discharged gas is measured. After the measurement, the discharged gas is conducted from the FT-IR 10 through an exhaust line 26 and introduced in a harmful substance removal apparatus 16. After harmful substances in the discharged gas are removed by the harmful substance removal apparatus 16, the discharged gas is emitted into the atmosphere.

In accordance with the present embodiment, IGA2000 manufactured by MIDAC Corporation is used as FT-IR 10. Also, for the measurement, a cell of one centimeter long is used to correct the temperature and the pressure. It is noted that the apparatus and cell to be used for the measurement are not limited to those listed above.

(Measurement Method)

<Measurement Steps>

Infrared absorption of the discharged gas introduced in the FT-IR 10 shown in FIG. 1 is measured mainly in accordance with the following steps (1)~(5).

(1) Selecting a process chemical material.

(2) Selecting a measurement target chemical material corresponding to the process chemical material.

(3) Designating expected concentration ranges for the process chemical material and the measurement target chemical material.

(4) Selecting libraries for the respective expected concentration ranges for the process chemical material and the measurement target chemical material.

(5) Analyzing data obtained by a gas infrared absorption spectrometry based on the libraries.

To perform the steps (1)~(5), FIG. 2 is used to select expected concentration ranges, and libraries to make calibration curves corresponding to the expected concentration ranges for the process chemical material and measurement target chemical materials. FIG. 2 schematically shows a calculation sheet that is used to select measurement target chemical materials by a process using a computer based on a selected process chemical material in the discharged gas. The calculation sheet is displayed on, for example, a display. In this case, the display is provided to display contents of the process performed by the computer. Alternatively, it can be included in an algorithm in the measurement apparatus.

The Intel Protocol lists, when components in a discharged gas including PFC are measured, $CF_4$, $CHF_3$, $C_2F_4$, $C_2F_6$, $C_3F_8$, $C_4F_8$, $C_5F_8$, HF, $SiF_4$, $NF_3$, $SF_6$ and $N_2O$ as examples of the process chemical material. Also, $CF_4$, $CHF_3$, $C_2F_4$, $C_2F_6$, $C_3F_8$, $C_4F_8$, $C_5F_8$, $COF_2$, HF, $SiF_4$, $OF_2$, $NF_3$, $SO_2$, $SF_6$, $SO_2F_2$, $SOF_2$, NO, $N_2O$, $NO_2$, CO and $CO_2$ are listed as examples of the measurement target chemical materials.

Measurement steps are described below.

(1) First, a process chemical material is selected. In the present embodiment, $C_4F_8$ used for generating gas plasma in the dry etching apparatus corresponds to a process chemical material. In the display screen shown in FIG. 2, materials that are expected to be included in the discharged gas are listed, and a process chemical material is selected from them.

(2) Next, measurement target chemical materials corresponding to the process chemical material are selected.

In the calculation sheet, measurement target chemical materials corresponding to a process chemical material are linked to one another in advance. When a process chemical material is selected in the displayed image shown in FIG. 2 (e.g., $C_4F_8$ in FIG. 2), measurement target chemical materials are automatically selected and displayed, as shown in FIG. 3.

(3) Then, expected concentration ranges for the process chemical material and the measurement target chemical materials are designated for each component. Also, expected concentration ranges are similarly designated for components that are expected to be contained in the discharged gas other than the process chemical material and the measurement target chemical materials (e.g., NO, $NO_2$ and the like in FIG. 3).

(4) The calculation sheet is linked to libraries corresponding to the expected concentration ranges of the respective components displayed on the display screen. In other words, the expected concentration ranges of the respective components are linked to the libraries. When an expected concentration range for each of the components is selected, a library corresponding to the expected concentration range is selected and displayed on the display screen.

In the meantime, each of the components contained in the discharged gas has a main peak region and an auxiliary peak region in its infrared absorption spectrum, as shown in Table 1 below. In Table 1, for each of the components, a range indicating a main peak region is indicated by a mark of double circles, and a range indicating an auxiliary peak region is indicated by a mark of a single circle. In Table 1, only main peak regions are shown for components other than $CF_4$, $CHF_3$ and $C_2F_6$.

TABLE 1

| Subject concentration | | Selected wave number (cm⁻¹) | | |
|---|---|---|---|---|
| $CF_4$ | | 1230–1305 | 2160–2200 | |
| | 0~100 ppm-m | ⊚ | | |
| | 100~ ppm-m | | ○ | |
| $CHF_3$ | | 1090–1247 | 1316–1437 | 2980–3080 |
| | 0~10 ppm-m | ⊚ | | |
| | 10~60 ppm-m | | ○ | |
| | 60~ ppm-m | | | ○ |
| $C_2F_4$ | | 1161–1212 | | |
| | 0~ ppm-m | ⊚ | | |
| $C_2F_6$ | | 1218–1290 | 1082–1162 | 2005–2095 |
| | 0~30 ppm-m | ⊚ | | |
| | 30~100 ppm-m | | ○ | |
| | 100~ ppm-m | | | ○ |
| $C_3F_8$ | | 956–1061 | | |
| | 0~ ppm-m | ⊚ | | |
| $C_4F_8$ | | 920–1020 | | |
| | 0~ ppm-m | ⊚ | | |
| $SF_6$ | | 910–1009 | | |
| | 0~ ppm-m | ⊚ | | |
| $NF_3$ | | 832–960 | | |
| | 0~ ppm-m | ⊚ | | |
| CO | | 2143–2246 | | |
| | 0~ ppm-m | ⊚ | | |
| $CO_2$ | | 2280–2390 | | |
| | 0~ ppm-m | ⊚ | | |
| $COF_2$ | | 1790–2015 | | |
| | 0~ ppm-m | ⊚ | | |
| $OF_2$ | | 755–1012 | | |
| | 0~ ppm-m | ⊚ | | |
| HF | | 4032–4080 | | |
| | 0~ ppm-m | ⊚ | | |
| $SiF_4$ | | 1000–1058 | | |
| | 0~ ppm-m | ⊚ | | |
| $SOF_2$ | | 700–878 | | |
| | 0~ ppm-m | ⊚ | | |

TABLE 1-continued

| Subject concentration | | Selected wave number (cm$^{-1}$) | |
|---|---|---|---|
| SO$_2$F$_2$ | | 1445–1545 | |
| | 0~ ppm-m | ◎ | |
| SO$_2$ | | 1290–1415 | |
| | 0~ ppm-m | ◎ | |
| NO | | 1757–1990 | |
| | 0~ ppm-m | ◎ | |
| NO$_2$ | | 1525–1791 | |
| | 0~ ppm-m | ◎ | |
| N$_2$O | | 1216–1338 | |
| | 0~ ppm-m | ◎ | |

In the meantime, the library described above includes calibration curve data for the main peak region and the auxiliary peak region respectively for each of the components in the gas. The calibration curve data is data representing the relation between concentrations and absorption areas. When the infrared absorption measurement of the present invention is conducted, a library corresponding to an expected concentration range is selected, and data analysis is conducted based on a calibration curve data corresponding to the library. In other words, when a library is selected, a peak region to be measured is selected, and data analysis is conducted based on a calibration curve data corresponding to the peak region. These libraries are described below.

FIG. 3 shows libraries selected according to the expected concentration ranges of the respective components. For example, when the expected concentration range of CF$_4$ is ~10 ppm-m, a library selected according to this expected concentration range is "CF4_10A". This library is set to perform data analysis for CF$_4$, using calibration curve data of a peak region of wave numbers of 1230–1305 cm$^{-1}$. Also, when the expected concentration range of CHF$_3$ is ~10 ppm-m, a library selected according to this expected concentration range is "TFM_10A". This library is set to perform data analysis for CHF$_3$, using calibration curve data of a peak region of wave numbers of 1090–1247 cm$^{-1}$.

Referring to FIG. 3, when the expected concentration range of CHF$_3$ is selected to be ~10 ppm-m, a library selected according to this expected concentration range is "TFM_10A". Here, as shown in FIG. 4, when the expected concentration range for CHF$_3$ is changed to 60~ppm-m, the library is also changed according to the expected concentration range, and a library of "TFM_60A" is newly selected.

It is noted that two or more libraries can be selected for one expected concentration range. For example, as shown in FIG. 5, when an expected concentration range of 10~60 ppm-m is selected for CHF$_3$, three libraries "TFM_10A", "16A" and "60A" are selected for the expected concentration range. The libraries "TFM_10A", "16A" and "60A" are set to perform data analysis for CHF$_3$, using calibration curve data of peak regions of wave numbers of 1090–1247 cm$^{-1}$, 1316–1437 cm$^{-1}$, and 2980–3080 cm$^{-1}$, respectively.

(5) Based on the libraries selected in a manner described above, an infrared absorption spectrometry is performed for the discharged gas. By performing data analysis based on the libraries, concentrations can be calculated based on absorption areas of the respective components.

<Optimization of Libraries>

Figure 6:
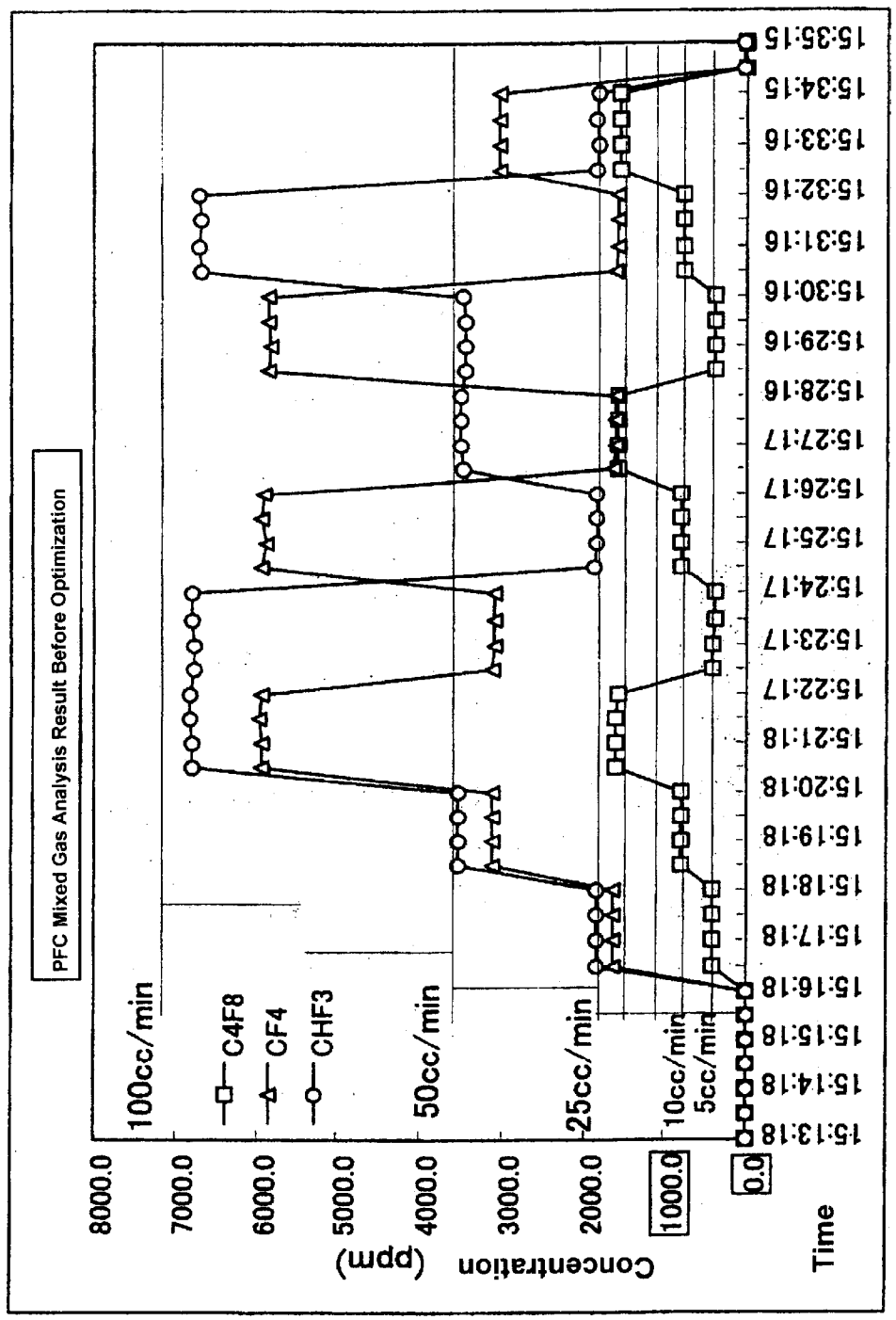
FIG. 6 shows changes in the concentration of each of the gases with the passage of time, which are obtained by data analysis using libraries with respect to a result of an infrared absorption spectrometry before optimization.

According to the procedure described above, a mixed gas of CHF$_3$, CF$_4$ and C$_4$F$_8$ is flowed while the mixing ratio of the gases is changed at every 120 seconds, and an infrared absorption spectrometry is performed for the mixed gas with the passage of time. For the measurement, as shown in Table 4, data analysis is conducted based on the calibration curve data of the main peak in the library for each of CHF$_3$, CF$_4$ and C$_4$F$_8$. FIG. 6 shows changes in the concentration of each of the gases with the passage of time, which are obtained by the data analysis. It is noted that the mixed gas of CHF$_3$, CF$_4$ and C$_4$F$_8$ is flowed while their concentrations are changed in nine different levels at every 120 seconds as shown in Table 2. Also, for the measurement, the mixed gas is mixed with Ar and thereafter diluted by a predetermined amount of N$_2$, and then the mixed gas is measured. Accordingly, the vertical axis in FIG. 6 indicates concentrations of the respective gases in the gas including Ar and N$_2$. Also, in FIG. 6, concentrations roughly calculated according to the flow quantity of CHF$_3$, CF$_4$ and C$_4$F$_8$ in the gas containing Ar and N$_2$ are indicated along the horizontal axis when CHF$_3$, CF$_4$ and C$_4$F$_8$ are flown at 5, 10, 25, 50 or 100 [cc/min], respectively.

TABLE 2

Assumed N$_2$ flow quantity: 14.36 l/min

| | Ar | C$_4$F$_8$ | CF$_4$ | CHF$_3$ |
|---|---|---|---|---|
| 1 | 100 | 5 | 25 | 25 |
| 2 | 100 | 10 | 50 | 50 |
| 3 | 100 | 20 | 100 | 100 |
| 4 | 200 | 5 | 50 | 100 |
| 5 | 200 | 10 | 100 | 25 |
| 6 | 200 | 20 | 25 | 50 |
| 7 | 400 | 5 | 100 | 50 |
| 8 | 400 | 10 | 25 | 100 |
| 9 | 400 | 20 | 50 | 25 |

Unit [cc/min.]

Referring to FIG. 6, for CHF$_3$ and C$_4$F$_8$, there is not a substantial difference between the concentration of the gas actually flowed and the concentration of the gas obtained by the measurement. In contrast, for CF$_4$, when the concentration is large (e.g., 100 cc/min.), the concentration of the actual flow deviated from the concentration obtained by the measurements. The following reasons (1) and (2) are considered for the deviation.

Figure 7:
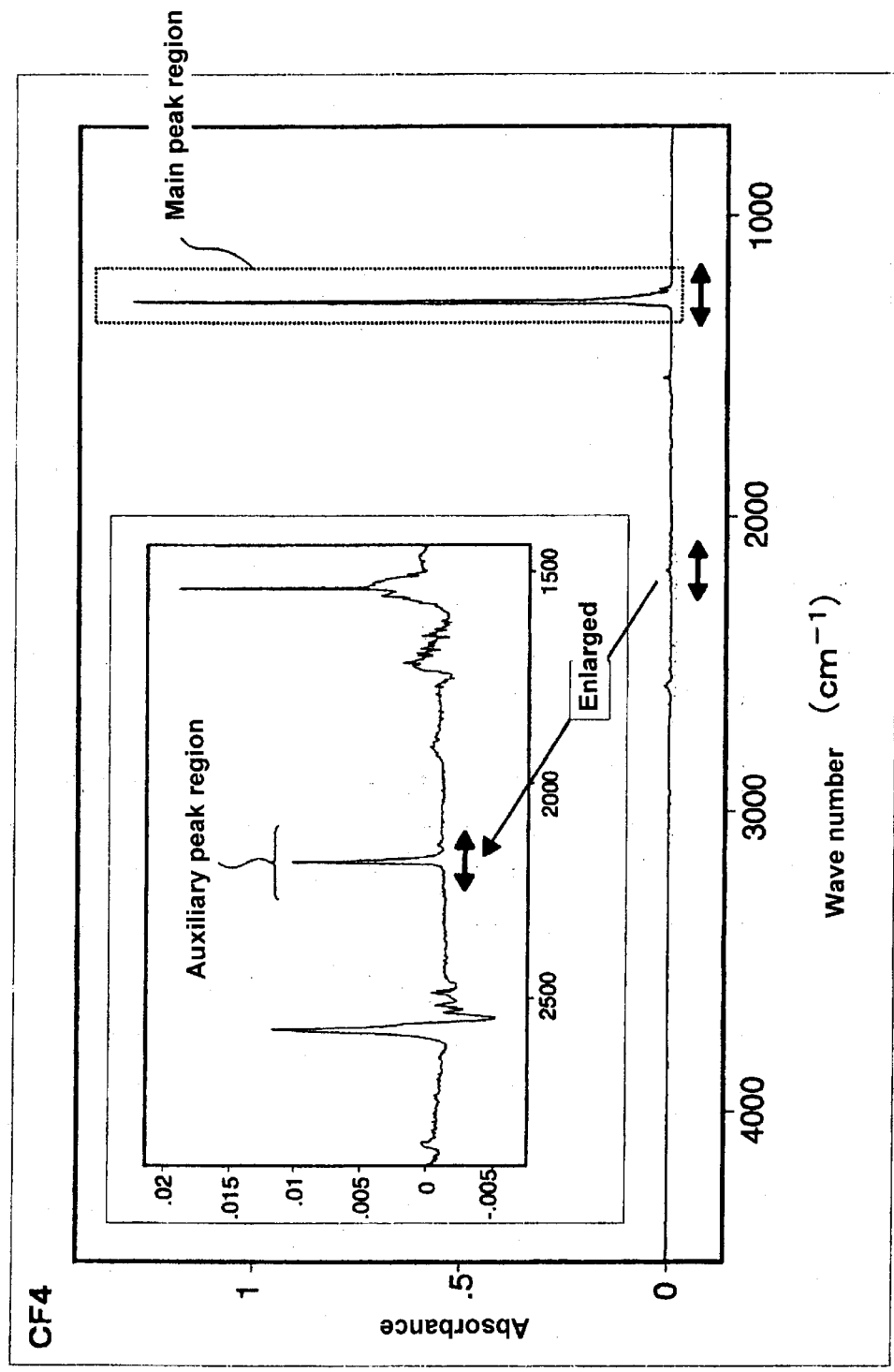
FIG. 7 shows a main peak region and an auxiliary peak region of $CF_4$.
Figure 8:
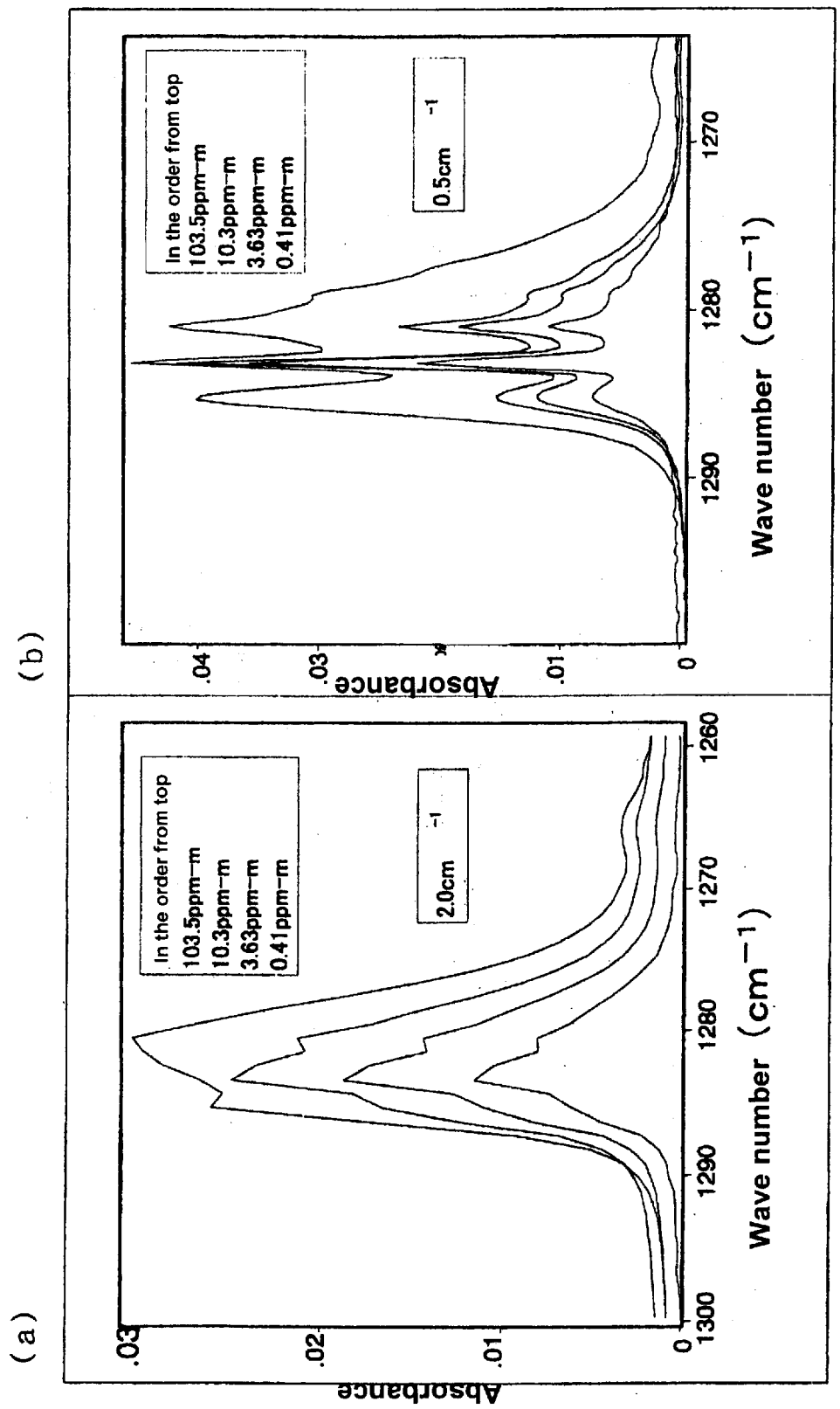
FIGS. 8(a) and 8(b) show an enlarged view of the main peak region of $CF_4$.

(1) As described above, each of the components in the discharged gas has a main peak region and an auxiliary peak region in its infrared absorption waveform, as shown in Table 1. For example, CF$_4$ has a main peak region in 1230–1305 cm$^{-1}$ as shown in Table 1 and FIG. 7, and an auxiliary peak region in 2160–2200 cm$^{-1}$. Furthermore, FIGS. 8(a) and (b) show enlarged views of the main peak region (1230–1305 cm$^{-1}$). FIG. 8 (b) shows the result measured with a resolution higher than that of FIG. 8(a). In FIG. 7, there appears to be a peak in the main peak region of CF$_4$. However, when enlarged, it is understood that a plurality of peaks are present in the main peak region of CF$_4$, as shown in FIGS. 8 (a) and (b). Therefore, in this case, when the absorbance is measured to calculate the concentration and a calibration curve is made while ignoring the presence of the plurality of peaks, the deviation may become large.

(2) FIGS. 8(a) and (b) show infrared absorption waveforms of the main peak region (1230–1305 cm$^{-1}$) for CF$_4$ having different concentrations, and more specifically, infrared absorption waveforms of the main peak region for CF$_4$ having concentrations of 103.5 ppm-m, 10.3 ppm-m, 3.63 ppm-m, and 0.41 ppm-m, respectively, in the order from a higher peak. In FIGS. 8(a) and (b), each area (light absorbing area) that is surrounded by the waveform and the horizontal axis (wave number) is proportional to the each concentration of CF$_4$. Accordingly, by referring to FIGS. 8(a) and (b), the concentration of CF$_4$ can be calculated based on the light absorption area.

In the main peak region for $CF_4$, the peak included in the waveform becomes higher as the concentration of $CF_4$ becomes greater from 0.41 ppm-m, 3.63 ppm-m, and 10.3 ppm-m, as shown in FIG. 8(b). However, when the concentration of $CF_4$ becomes to be 103.5 ppm-m, the highest peak does not become higher in proportion to the increase of the concentration, and becomes saturated at a certain absorbance. Therefore, when calibration curve data based on the main peak region is used, an accurate concentration may not be calculated based the light absorbing area at a relatively large concentration of $CF_4$ because the light absorbing area is not proportional to the concentration of $CF_4$.

Because of the reasons (1) and (2) described above, for example, for $CF_4$, if calibration curve data of the main peak region in the library is used as it is in analyzing data based on the library for each gas, a deviation may occur between the actual concentration and the concentration obtained by measurement. In order to reduce the deviation and obtain an accurate concentration, the library needs to be optimized. The optimization of the library is described below. Selection of Library Depending on Concentration As described above, for example, $CF_4$ has a main peak region in 1230–1305 $cm^{-1}$, and an auxiliary peak region in 2160–2200 $cm^{-1}$, as shown in Table 1 and FIG. 7. In the case of $CF_4$, as described above, when calibration curve data based on the main peak region is used to analyze data, an accurate concentration may not be calculated based on the light absorbing area at a relatively large concentration of $CF_4$ because the light absorbing area is not proportional to the concentration of $CF_4$.

Figure 9:
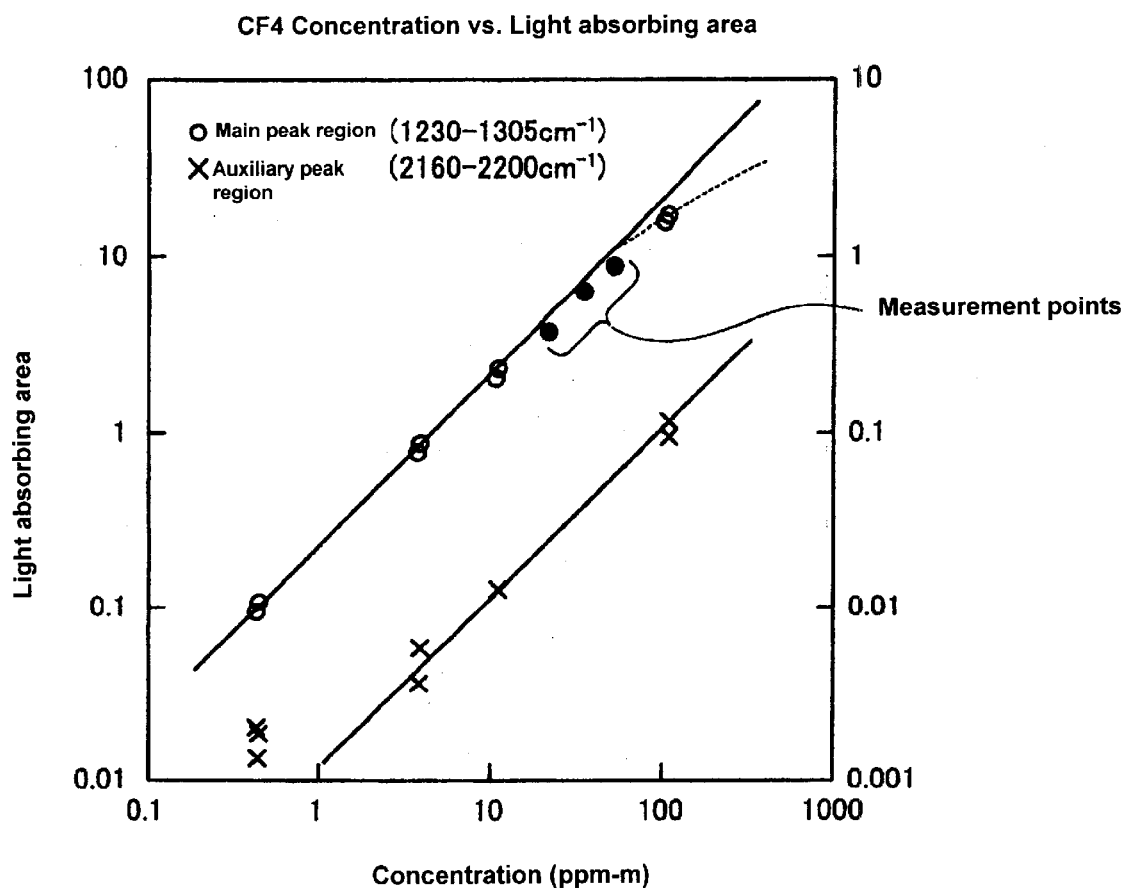
FIG. 9 shows relationships between concentrations and light absorption areas (calibration curves) in the main peak region and the auxiliary peak region of $CF_4$.

Relations (calibration curves) between concentrations and light absorbing areas for $CF_4$ in the main peak region and the auxiliary peak region are shown in FIG. 9. Referring to FIG. 9, in the calibration curve for the main peak region in a range where the concentration of $CF_4$ is small, the light absorbing area becomes greater in proportion to the concentration of $CF_4$. In contrast, in a region where the concentration of $CF_4$ is large (i.e., in the area where the concentration is 100 ppm-m or greater), the light absorbing area is not proportional to the concentration of $CF_4$, as described above. In other words, the calibration curve for the main peak region has excellent linearity in a region where the concentration of $CF_4$ is small, but has a lower linearity in a region where the concentration of $CF_4$ is large. In FIG. 9, the calibration curve for the main peak region is presented with calibrations on a vertical axis (light absorption areas) on the left side of the graph and the calibration curve for the auxiliary peak region is presented with calibrations on a vertical axis on the right side of the graph.

To solve the problems described above, when the concentration of $CF_4$ in the gas is assumed to be large, in other words, when the concentration of $CF_4$ in the gas is assumed to be included in the region where the linearity of the calibration curve for the main peak region is small, the concentration is determined using the calibration curve for the auxiliary peak region. In other words, data is analyzed based on the data (calibration curve data) of the calibration curve for the auxiliary peak region. As a result, the concentration of $CF_4$ can be accurately calculated.

In the meantime, in the calibration curve for the auxiliary peak region in a range where the concentration of $CF_4$ is large, the light absorbing area becomes greater in proportion to the concentration of $CF_4$. In contrast, in a region where the concentration of $CF_4$ is small (i.e., in the area where the concentration is less than 1 ppm-m), the light absorbing area is not proportional to the concentration of $CF_4$. In other words, the calibration curve for the auxiliary peak region has excellent linearity in a region where the concentration of $CF_4$ is large, but has a lower linearity in a region where the concentration of $CF_4$ is small. One of the reasons is that, as shown in FIG. 7, $CF_4$ has peaks in its auxiliary peak region, which are substantially shorter than the peak in the main peak region. Therefore, in the region where the concentration of $CF_4$ is small, it is difficult to accurately read peaks of $CF_4$ because of the influence of noises, and thus the deviation is believed to become larger. Therefore, in the region where the concentration of $CF_4$ is small, it is believed that an accurate calibration curve based on the auxiliary peak region is difficult to obtain.

To solve the problems described above, when the concentration of $CF_4$ in the gas is assumed to be small, in other words, when the concentration of $CF_4$ in the gas is assumed to be included in the region where the linearity of the calibration curve for the auxiliary peak region is small, the concentration is determined using the calibration curve for the main peak region. In other words, data is analyzed based on the data (calibration curve data) of the calibration curve for the main peak region. As a result, the concentration of $CF_4$ can be accurately calculated.

Figure 10:
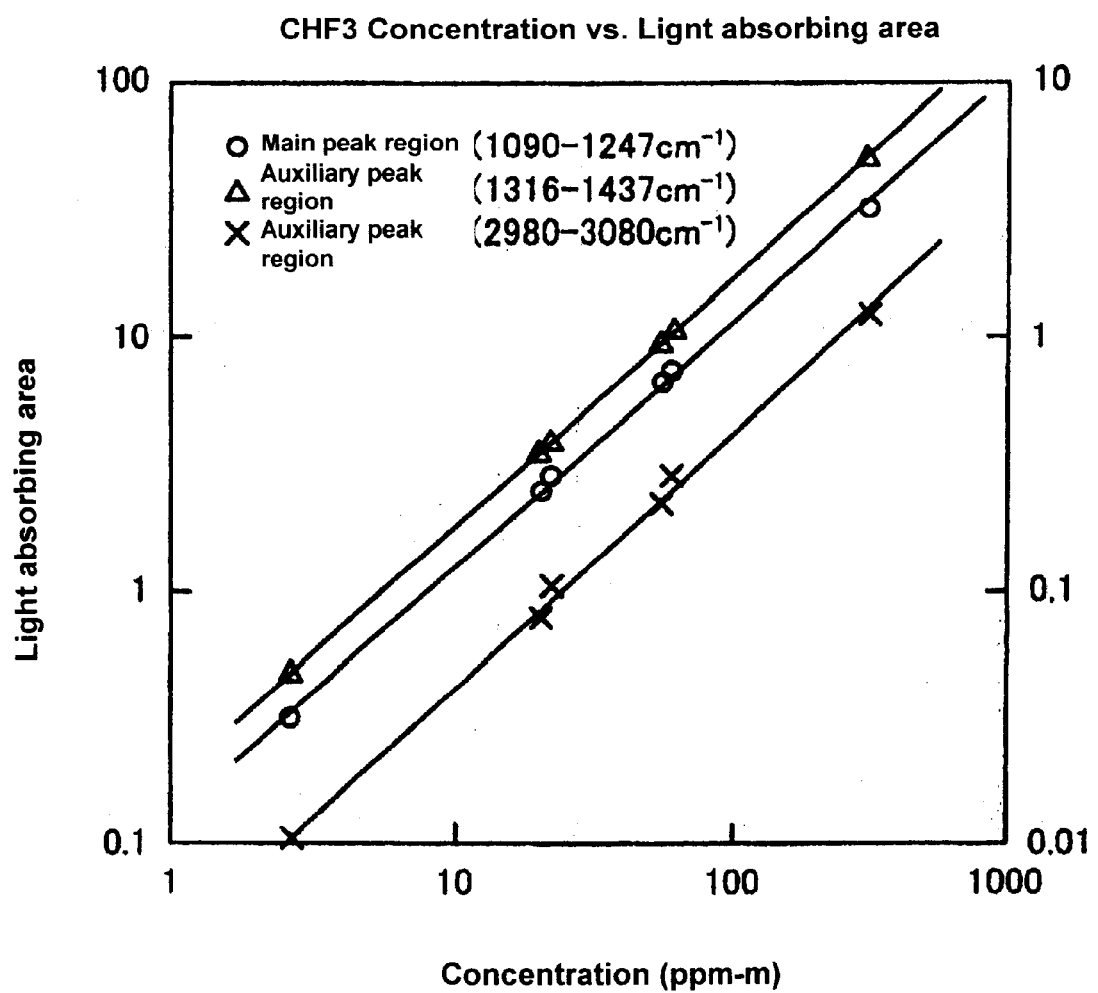
FIG. 10 shows relationships between concentrations and light absorption areas (calibration curves) in the main peak region and the auxiliary peak region of $CHF_3$.
Figure 11:
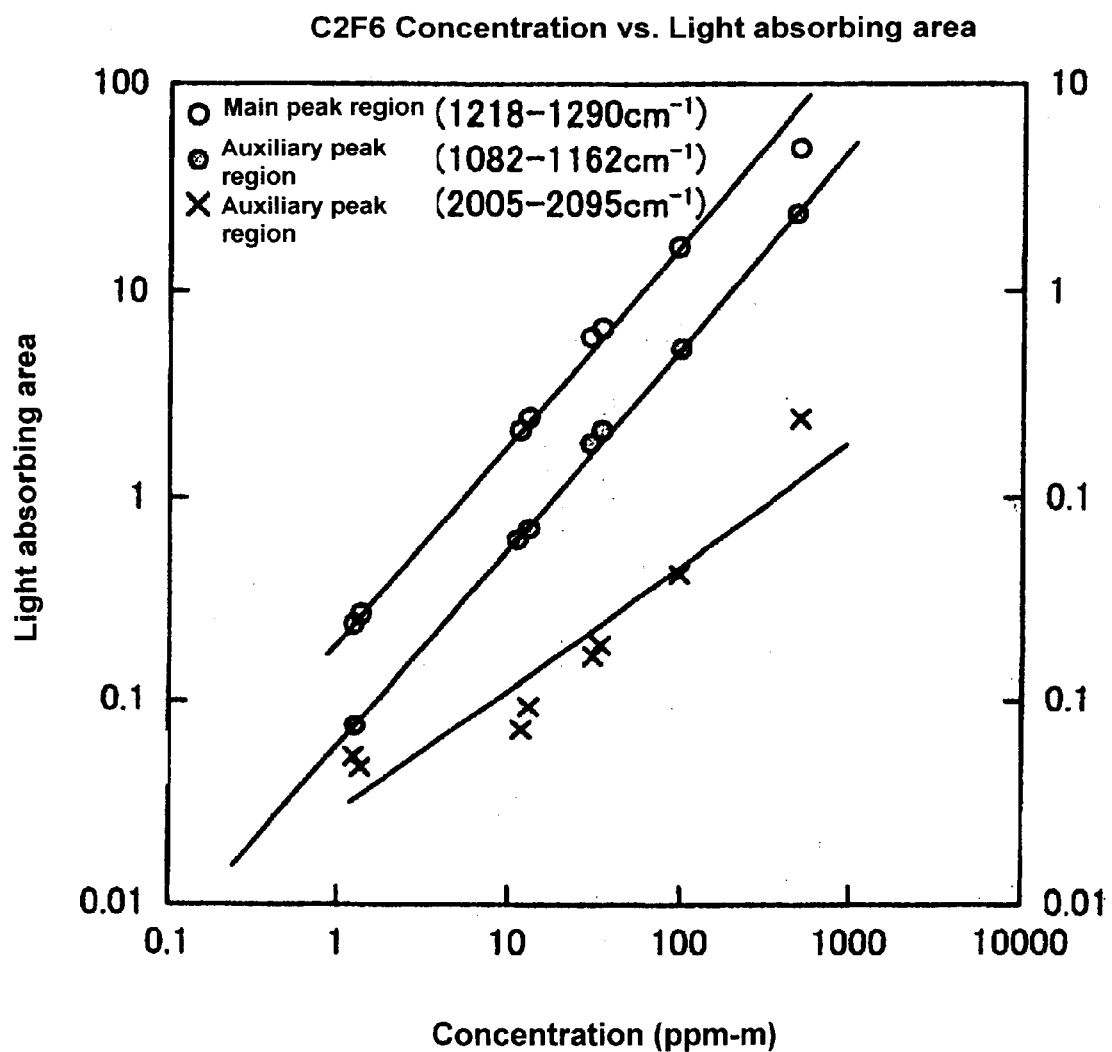
FIG. 11 shows relationships between concentrations and light absorption areas (calibration curves) in the main peak region and the auxiliary peak region of $C_2F_6$.

FIG. 10 and FIG. 11 show calibration curves for the main peak regions and the auxiliary peak regions for $CHF_3$ and $C_2F_6$, respectively, in a similar manner as $CF_4$. The calibration curves for $CHF_3$, for both of the main peak region and the auxiliary peak region, have excellent linearity. On the other hand, with respect to $C_2F_6$, the calibration curve for the main peak region has excellent linearity in a region where the concentration is small, in a similar manner as $CF_4$. On the other hand, in the range where the concentration is large, the calibration curve for the auxiliary peak region has better linearity than that of the calibration curve for the main peak region. Therefore, in order to accurately calculate the concentration of $C_2F_6$, the concentration may preferably be determined using the calibration curve for the main peak region in the range where the concentration thereof in the gas is small, and may preferably be determined using the calibration curve for the auxiliary peak region in the range where the concentration thereof in the gas is large. It is noted that, in FIG. 10, the calibration curve for the main peak region is presented with calibrations on a vertical axis (light absorption areas) on the left side of the graph, and the two calibration curves for the auxiliary peak regions are presented with calibrations on a vertical axis on the right side of the graph. Also, in FIG. 11, the calibration curves for the main peak region and the auxiliary peak region (1082–1162 $cm^{-1}$) are presented with calibrations on a vertical axis (light absorption areas) on the left side of the graph, and the calibration curve for the auxiliary peak region (2005–2095 $cm^{-1}$) is presented with calibrations on a vertical axis on the right side of the graph.

2. Increase of Measuring Points

As described above, when the calibration curve based on the main peak region is used for measurement of the concentration of, for example, $CF_4$, and the concentration is close to 100 ppm-m, the highest peak among the peaks contained in the main peak region becomes saturated at a certain absorbance, the light absorbing area becomes not proportional to the concentration of $CF_4$, and the linearity of the calibration curve representative of the relation between the concentration and the absorbance becomes lower. As a result, an accurate concentration may not be calculated based on the absorbance.

To solve the problems, for a portion of the calibration curve based on the main peak region having lower linearity, a correction to increase measurement points adjacent to the area is performed with respect to the calibration curve. For example, in the case of $CF_4$, at least three more measurement points are provided in the concentration range of 10–100 ppm-m, as shown in FIG. 9. Locations where measurement points are provided, the concentration range and the number thereof are appropriately adjusted depending on gases. By performing the correction, the accuracy based on the main peak region can be enhanced. By analyzing data based on data for the calibration curve (calibration curve data) that is corrected by the measurement method described above, the concentration of $CF_4$ can be accurately calculated.

On the other hand, for a portion of the calibration curve having high linearity, one or two measurement points in the high linearity portion may be used to make the calibration curve. For example, referring to FIG. 9, when a calibration curve for the main peak region of $CF_4$ is made, for a portion among the calibration curve having high linearity (in the range of 0.1–10 ppm-m), one or two measurement points may be used to make the calibration curve. In the manner described above, a highly accurate calibration curve can be made with fewer measurement points for a portion having high linearity.

Figure 12:
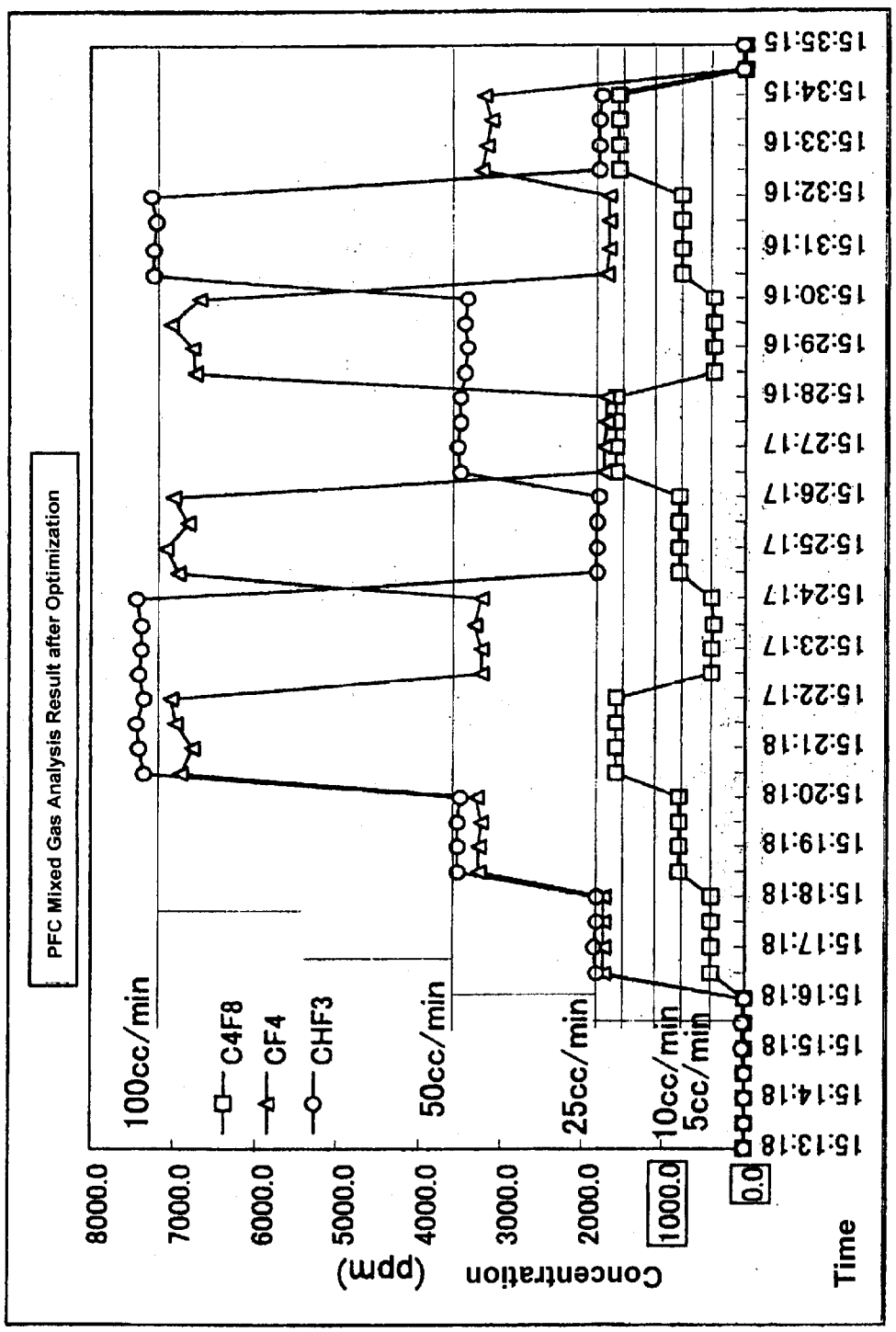
FIG. 12 shows changes in the concentration of each of the gases with the passage of time, which are obtained by data analysis using optimized libraries with respect to a result of an infrared absorption spectrometry.

Data analysis is conducted for measurement results shown in FIG. 6, using the calibration curve that is optimized by the method described above. FIG. 12 shows changes with the passage of time in the concentration of each of the gases obtained by the data analysis. For the optimized calibration curves, data for the calibration curves for both of the main peak region and the auxiliary peak region is used for $CHF_3$, as shown in Table 3. Furthermore, with respect to $CF_4$, data for the calibration curve after correction is used to perform analysis.

TABLE 3

| Gas Type | Wave Number ($cm^{-1}$) | Concentration (ppm-m) | | |
|---|---|---|---|---|
| $CF_4$ | 1230–1305 | 3.77 | 10.3 | 103.5 |
| $CHF_3$ | 1090–1247 | 2.65 | | |
| | 1316–1437 | 57.5 | | |
| | 2980–3080 | 313.5 | | |
| $C_4F_8$ | 920–1020 | 77.7 | 174.3 | |

TABLE 4

| Gas Type | Wave Number ($cm^{-1}$) | Concentration (ppm-m) | | |
|---|---|---|---|---|
| $CF_4$ | 1230–1305 | 3.77 | 10.3 | 103.5 |
| $CHF_3$ | 1090–1247 | 2.65 | 62.2 | 313.5 |
| $C_4F_8$ | 920–1020 | 77.7 | 174.3 | |

Here, the graph shown in FIG. 6 that is obtained by the data analysis using the calibration curves before optimization is compared to the graph shown in FIG. 12 that is obtained by the data analysis using the optimized calibration curves. As a result, for both of $CHF_3$ and $CF_4$, values that are close to the concentrations of the gases actually flown are obtained particularly in the region where the concentration is high (100 cc/min.).

As described above, by optimizing the calibration curve for each of the gases in the discharged gas, the concentration of each of the gases can be more accurately measured.

In the case of $CF_4$ described above, when the expected concentration range of $CF_4$ in the discharged gas is included in the region where the linearity of the calibration curve data for the main peak region is small, the concentration is determined using the calibration curve data for the auxiliary peak region. However, depending on chemical material that is used, when the expected concentration range of the chemical material is included in the region where the linearity of the calibration curve data for the auxiliary peak region is small, the concentration may be determined using the calibration curve data for the main peak region.

<Measurement Method>

Next, a method is described for measuring each of components contained in the discharged gas based of absorption waveforms obtained by measuring the discharged gas by a FT-IR.

Figure 13:
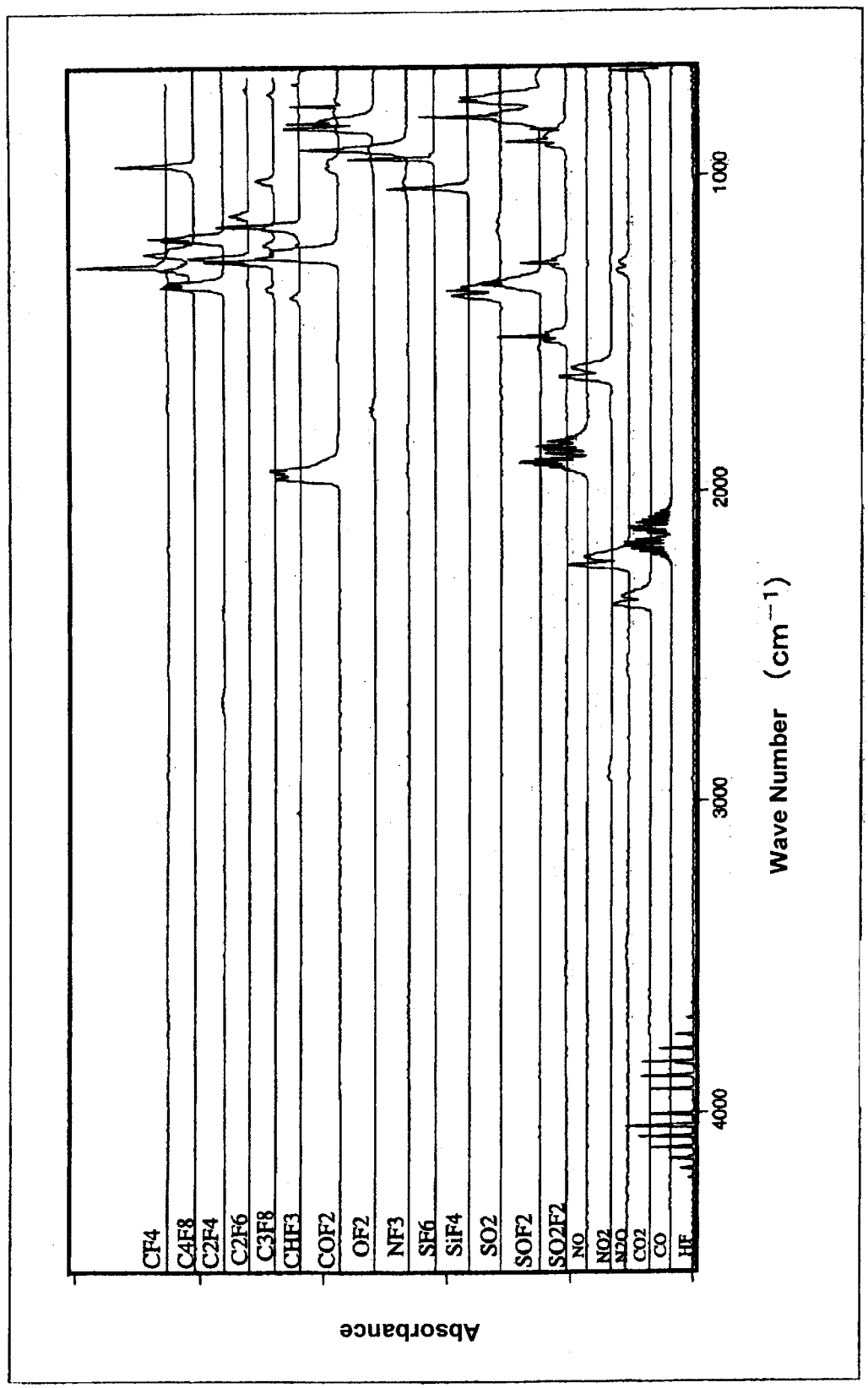
FIG. 13 shows infrared absorption waveforms of components contained in a discharged gas containing CFC.

Since actually discharged gas contains a plurality of components, an absorption waveform obtained by the measurement is a composite waveform of absorption waveforms of the plural components. FIG. 13 shows infrared absorption waveforms of gases that are assumed to be included in the discharged gas containing PFC. An absorption waveform that is obtained by measurement of the actual discharged gas is a composite waveform of the waveforms shown in FIG. 13. Therefore, when the concentration of each of the compositions in the discharged gas is to be measured, and if peaks of different compositions concur with one another, it is difficult to calculate the concentrations, and there are occasions in that accurate concentrations are difficult to measure.

Figure 14:
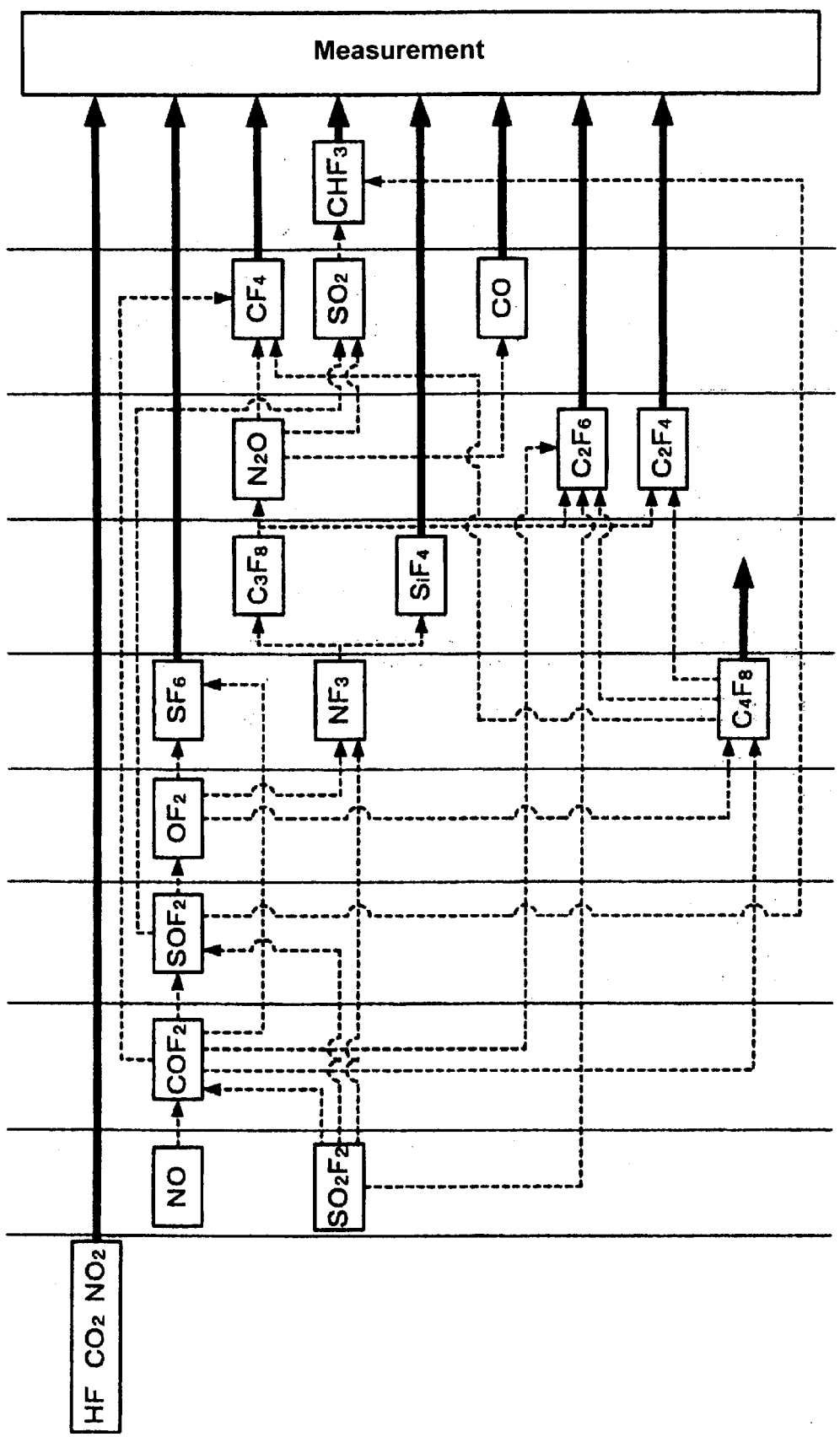
FIG. 14 is a schematic showing one example of a measurement method in accordance with the present invention.

In one embodiment of the present invention, when data analysis is performed based on absorption waveforms obtained by infrared absorption spectrometry that is conducted on the gas, those of the components of the gas having peaks that do not overlap peaks of the other components are measured on priority basis, and the peaks of those components are successively subtracted from the absorption waveforms to thereby determine the concentration of each of the components. This measurement method is described with reference to FIGS. 13 and 14. FIG. 14 shows the steps of the measurement method. In FIG. 14, the range of each thick solid line with an arrow that extends horizontally is a range in which each of the gases can be measured. Arrows with broken lines are presented for describing the steps, and thin solid lines (vertical lines) are presented for dividing the steps.

(1) First, infrared absorption waveforms (libraries) of all gases that are assumed to be included in the discharged gas are prepared. In this method, when gases other than the assumed gases are included in the discharged gas, the peaks corresponding to the remaining gases are left when the measurement is completed.

The infrared absorption waveforms of the gases are compared to one another, and those among the assumed gases having peaks that do not overlap peaks of any of the other gases are determined and are subtracted from the absorption waveforms. Referring to FIG. 13, HF, $CO_2$ and $NO_2$ correspond to those gases having peaks that do not overlap peaks of any of the other gases. These gases are subtracted from the absorption waveforms to measure the gases, respectively. Even when these gases are subtracted from the absorption waveforms, they do not affect the shapes of the peaks of the other gases. Therefore, they can be subtracted in a later step instead of being subtracted from the absorption waveforms at this moment.

(2) Next, components in the gas having peaks that do not overlap peaks of any of the other components are measured on priority basis, and the peaks of the components are subtracted from the absorption waveforms. NO and $SO_2F_2$ correspond to these components in FIG. 13, and therefore peaks of NO and $SO_2F_2$ are subtracted from the absorption waveforms to measure them, respectively. New absorption waveforms obtained by subtracting the peaks of NO and $SO_2F_2$ from the absorption waveforms include a peak of $COF_2$, which is a peak that does not overlap peaks of the other components. Accordingly, the peak of $COF_2$ is subtracted from the absorption waveforms, and measurement thereof is conducted. As a result, new absorption waveforms are obtained. Thereafter, according to the steps shown in FIG. 14, these steps are repeated until peaks are eliminated from the absorption waveforms. More specifically, a peak of $SOF_2$ is subtracted from the absorption waveforms obtained by the steps described above, and measurement thereof is conducted. Then, a peak of $OF_2$ is subtracted from the absorption waveforms obtained by the step described above, and measurement thereof is conducted. Then, peaks of $SF_6$, $NF_3$ and $C_4F_8$ are subtracted from the absorption waveforms obtained by the step described above, and measurements thereof are conducted. It is noted that $SF_6$ may be measured in any one of the steps to be performed later than the present step, instead of being measured in the present step. Also, it is noted that $C_4F_8$ can be measured in any one of the steps to be performed later than the present step but before a step in which $N_2O$, $C_2F_6$ and $C_2F_4$ are measured, instead of being measured in the present step. Then, peaks of $C_3F_8$ and $SiF_4$ are subtracted from the absorption waveforms obtained by the step described above, and measurements thereof are conducted, respectively. $SiF_4$ may be measured in any one of the steps to be performed later than the present step, instead of being measured in the present step. Then, peaks of $N_2O$, $C_2F_6$, and $C_2F_4$ are subtracted from the absorption waveforms obtained by the step described above, and measurements thereof are conducted. It is noted that $C_2F_6$ and $C_2F_4$ may be measured in any one of the steps to be performed later than the present step, instead of being measured in the present step. Then, peaks of $CF_4$, $SO_2$ and CO are subtracted from the absorption waveforms obtained by the step described above, and measurements thereof are conducted. It is noted that $CF_4$ and CO may be measured in any one of the steps to be performed later than the present step, instead of being measured in the present step. Then, $CHF_3$ is measured from the absorption waveforms obtained by the step described above.

In a manner described above, the data is analyzed, and the components are successively measured. It is noted that the steps shown in FIG. 14 is one example, and steps to subtract peaks are appropriately determined based on components that are included in the discharged gas.

By the method described above, the concentration of each of the components can be accurately measured, even when peaks of the components concur with one another or overlap one another.

<Correction Gas>

Also, when an infrared absorption spectrometry is performed on gas, one or more components in the gas may be used as correction gases. By this method, highly accurate correction can be performed.

Here, a plurality of values for concentrations of the correction gases to be used for correction may preferably be set at equal intervals in logarithmic values of the concentrations. When one of the multiple correction gases to be used for correction having the highest concentration is defined as a reference (=1), correction gases having concentrations of $1, 1/x, 1/x^2, 1/x^3, 1/x^4, \ldots 1/x^n$ (n is any number) from the order of higher concentration are successively used. For example, when one of the multiple correction gases to be used for correction having the highest concentration has a concentration of a, the other correction gases may preferably have concentrations of, from the order of higher concentration, $a/x, a/x^2, a/x^3, a/x^4, \ldots a/x^n$, respectively. Furthermore, when one of the multiple correction gases to be used for correction having the highest concentration has a concentration of "a", a correction gas having the smallest concentration that is about "a/20" may preferably be used, and in this case, "n" may preferably be, for example, 4~5.

By the method described above, measurement points can be disposed at equal intervals on a logarithmic scale, with the result that highly accurate calibration curves can be made with fewer measurement points.

In particular, when $CF_4$ or $SF_6$ is selected as a correction gas, a calibration curve representing absorption areas to concentrations with respect to a main peak region of the correction gas may be made, and a correction may preferably be made at a portion having excellent linearity in the calibration curve with respect to the main peak region.

As described above, in accordance with a method for measuring greenhouse gases using an infrared absorption spectrometer in accordance with the present invention, concentrations of components in a discharged gas can be correctly measured with a simpler method and a higher reproducibility.

What is claimed is:

1. A method for measuring greenhouse gases using an infrared absorption spectrometer, the method comprising the steps of:
   selecting a process chemical material;
   selecting a measurement target chemical material corresponding to the process chemical material:
      designating expected concentration ranges for the process chemical material and the measurement target chemical material;
      selecting libraries for the respective expected concentration ranges for the process chemical material and the measurement target chemical material; and
      analyzing data obtained by gas infrared absorption spectrometry based on the libraries.

2. The method for measuring greenhouse gases using an infrared absorption spectrometer according to claim 1, further comprising the steps of:
   making a library formed of absorbance data for a plurality of known concentrations for each chemical material in the gas;
   making calibration curve data with respect to concentration-absorption area for a main peak region and an auxiliary peak region for the each chemical material in the gas based on the library; and
   analyzing data obtained by the gas infrared absorption spectrometry based on the calibration curve data, such that when the expected concentration range of each composition among the gas is included in a region where a linearity of the calibration curve data for the main peak region is small, the concentration is determined using the calibration curve data for the auxiliary peak region.

3. The method for measuring greenhouse gases using an infrared absorption spectrometer according to claim 2, further including determining the concentration using both of the calibration curve data for the main peak region and the calibration curve data for the auxiliary peak region.

4. The method for measuring greenhouse gases using an infrared absorption spectrometer according to claim 1, further comprising the steps of:
   making a library formed of absorbance data for a plurality of known concentrations for each chemical material in the gas;

making calibration curve data with respect to concentration-absorption area for a main peak region and an auxiliary peak region for the each chemical material in the gas based on the library; and analyzing data obtained by the gas infrared absorption spectrometry based on the calibration curve data, such that when the expected concentration range of each composition among the gas is included in a region where a linearity of the calibration curve data for the auxiliary peak region is small, the concentration is determined using the calibration curve data for the main peak region.

5. The method for measuring greenhouse gases using an infrared absorption spectrometer according to claim 1, the selecting a process chemical material step including selecting the process chemical material including at least one of $CF_4$, $CHF_3$, $C_2F_4$, $C_2F_6$, $C_3F_8$, $C_4F_8$, $C_5F_8$, HF, $SiF_4$, $NF_3$, $SF_6$ and $N_2O$.

6. The method for measuring greenhouse gases using an infrared absorption spectrometer according to claim 1, the selecting a measurement target chemical material step including selecting the measurement target chemical material including at least one of $CF_4$, $CHF_3$, $C_2F_4$, $C_2F_6$, $C_3F_8$, $C_4F_8$, $C_5F_8$, $COF_2$, HF, $SiF_4$, $OF_2$, $NF_3$, $SO_2$, $SF_6$, $SO_2F_2$, $SOF_2$, NO, $N_2O$, $NO_2$, CO and $CO_2$.

7. A method for measuring greenhouse gases using an infrared absorption spectrometer according to claim 1, the gas including at least one of $CF_4$, $CHF_3$, $C_2F_4$, $C_2F_6$, $C_3F_8$, $C_4F_8$, $C_5F_8$, $COF_2$, HF, $SiF_4$, $OF_2$, $NF_3$, $SO_2$, $SF_6$, $SO_2F_2$, $SOF_2$, NO, $N_2O$, $NO_2$, CO and $CO_2$.

8. A method for measuring greenhouse gases using an infrared absorption spectrometer, comprising the steps of:

when data for gas obtained by an infrared absorption spectrometry is analyzed, making a calibration curve representing absorption areas with respect to concentrations for each of a main peak region and an auxiliary peak region for each component in the gas; and when a concentration of each composition among the gas is expected to be included in a region where a linearity of the calibration curve for the main peak region is small, determining the concentration using the calibration curve data for the auxiliary peak region.

9. The method for measuring greenhouse gases using an infrared absorption spectrometer according to claim 8, further including determining the concentration using both of the calibration curve for the main peak region and the calibration curve for the auxiliary peak region.

10. The method for measuring greenhouse gases using an infrared absorption spectrometer according to claim 8, further including, for a portion of the calibration curve having a low linearity, performing a correction to increase measurement points adjacent the portion with respect to the calibration curve.

11. The method for measuring greenhouse gases using an infrared absorption spectrometer according to claim 8, further including, for a portion of the calibration curve having a high linearity, making the calibration curve using one measurement point or two measurement points in the portion having a high linearity.

12. A method for measuring greenhouse gases using an infrared absorption spectrometer, comprising the steps of:

when data for gas obtained by an infrared absorption spectrometry is analyzed, making a calibration curve representing an absorption area with respect to concentration for each of a main peak region and an auxiliary peak region for each component in the gas; and when a concentration of each composition among the gas is expected to be included in a region where a linearity of the calibration curve for the auxiliary peak region is small, determining the concentration using the calibration curve for the main peak region.

13. A method for measuring greenhouse gases using an infrared absorption spectrometer, comprising the steps of:

when data is analyzed based on an absorption waveform for a gas obtained by an infrared absorption spectrometry, measuring components on priority basis, among components in the gas, having peaks that do not overlap peaks of the other components;

successively subtracting the peaks of the components from the absorption waveform:

(a) subtracting peaks of NO and $SO_2F_2$ from the absorption waveform of the gas to measure NO and $SO_2F_2$;

(b) subtracting a peak of $COF_2$ from the absorption waveform obtained in the step (a) to measure $COF_2$;

(c) subtracting a peak of $SOF_2$ from the absorption waveform obtained in the step (b) to measure $SOF_2$;

(d) subtracting a peak of $OF_2$ from the absorption waveform obtained in the step (c) to measure $OF_2$;

(e) subtracting peaks of $SF_6$, $NP_3$ and $C_4F_8$ from the absorption waveform obtained in the step (d) to measure $SF_6$, $NP_3$ and $C_4F_8$, respectively;

(f) subtracting peaks of $C_3F_8$ and $SiF_4$ from the absorption waveform obtained in the step (e) to measure $C_3F_8$ and $SiF_4$, respectively;

(g) subtracting peaks of $N_2O$, $C_2F_6$ and $C_2F_4$ from the absorption waveform obtained in the step (f) to measure $N_2O$, $C_2F_6$ and $C_2F_4$, respectively;

(h) subtracting peaks of $CF_4$, $SO_2$ and CO from the absorption waveform of the gas obtained in the step (g) to measure $CF_4$, $SO_2$ and CO, respectively;

(i) measuring $CHF_3$ from the absorption waveform obtained in the steps (a)~(h); and (j) subtracting peaks of HF, $CO_2$ and $NO_2$ from any of the absorption waveform of the gas and the absorption waveforms of the gas obtained in the steps (a)~(i).

14. The method for measuring greenhouse gases using an infrared absorption spectrometer according to claim 13, further comprising at least one of the following (1)~(8) steps:

(1) measuring HF, $CO_2$ and $NO_2$ by any one of the steps (a)~(i) instead of the step (j), or by the step that is different from the steps (a)~(i) but is conducted before the step (j);

(2) measuring $SF_6$ by any one of the steps (f)~(j) instead of the step (e), or by the step that is different from the steps (f)~(j) but is conducted after the step (e);

(3) measuring $CF_4$ by the step (i) or the step (j) instead of the step (h), or by the step that is different from the step (i) or the step (j) but is conducted after the step (h);

(4) measuring $SiF_4$ by any one of the steps (g)~(j) instead of the step (f), or by the step that is different from the steps (g)~(j) but is conducted after the step (f);

(5) measuring CO by the step (i) or the step (j) instead of the step (h), or by the step that is different from the step (i) or the step (j) but is conducted after the step (h);

(6) measuring $C_2F_6$ by any one of the steps (h)~(j) instead of the step (g), or by the step that is different from the steps (h)~(j) but is conducted after the step (g);

(7) measuring $C_2F_4$ by any one of the steps (h)~(j) instead of the step (g), or by the step that is different from the steps (h)~(j) but is conducted after the step (g); and (8) measuring $C_4F_8$ by the step (f) instead of the step (e), or by the step that is different from the step (f) but is conducted after the step (d) but before the step (g).

15. A method for measuring greenhouse gases using an infrared absorption spectrometer comprising:

conducting infrared absorption spectrometry for a gas;

using one or more of components in the gas as correction gases; and setting a plurality of values for concentrations of the correction gases to be used for correction at equal intervals in logarithmic values of the concentrations.

16. A method for measuring greenhouse gases using an infrared absorption spectrometer comprising:

conducting infrared absorption spectrometry for a gas;

using one or more of components in the gas as correction gases;

when $CF_4$ or $SF_6$ is selected as the correction gas, making a calibration curve representing absorption areas for concentrations with respect to a main peak region regarding the correction gas; and performing correction at portion having excellent linearity in the calibration curve with respect to the main peak region.

* * * * *